United States Patent [19]

Giering et al.

[11] 4,301,372
[45] Nov. 17, 1981

[54] PORTABLE FLUORESCENCE INSTRUMENT

[75] Inventors: Linda P. Giering, Harvard; John T. Brownrigg, Carlisle, both of Mass.

[73] Assignee: Baird Corporation, Bedford, Mass.

[21] Appl. No.: 148,795

[22] Filed: May 12, 1980

[51] Int. Cl.³ .......................... G01N 21/64; G01J 3/30
[52] U.S. Cl. .................................. 250/461 R; 356/317
[58] Field of Search .................. 250/372, 458, 461 R; 356/317, 318

[56] References Cited

U.S. PATENT DOCUMENTS

| | | | |
|---|---|---|---|
| 2,866,904 | 12/1958 | Hoellerich et al. | 250/461 R |
| 3,832,555 | 8/1974 | Ohnishi | 250/458 |
| 3,975,098 | 8/1976 | West | 250/461 R |
| 4,031,398 | 6/1977 | Callis et al. | 250/461 R |

Primary Examiner—Alfred E. Smith
Assistant Examiner—Janice A. Howell
Attorney, Agent, or Firm—Morse, Altman, Oates & Dacey

[57] ABSTRACT

A portable fluorescence instrument characterized by ultraviolet excitation optics and fluorescence spectral optics, particularly adapted for analysis of oil samples. The excitation optics include circuitry that adapts the instrument for field exploration by using low voltage power obtainable either from an internal rechargeable power source or from a conventional power source or from a conventional automobile battery. The fluorescence optics include a density step tablet that modulates the fluorescence intensity resulting in a spectral display characteristic of the particular sample. The spectral display is recorded on an instant film for on-site analysis.

12 Claims, 9 Drawing Figures

WAVE LENGTH (nm)

PORTABLE FLUORESCENCE INSTRUMENT

BACKGROUND OF THE INVENTION

1. Field of the Invention

The present invention relates to fluorescence instruments for analysis of oil samples and, more particularly, is directed towards a portable fluorescence instrument for on-site identification of oil samples and hazardous materials by recording the sample fluorescence spectrum on an instant film.

2. The Prior Art

Spectrometers are complex instruments that do not lend themselves to field use requiring on-site analysis of samples. Rather, samples taken in the field have to be brought to a laboratory equipped with a spectrometer to do the analysis. This results in delay and added expense. Such delay is particularly undesirable when trying to combat the effect of an oil spill on a beach far away from the laboratory. The delay attendant upon such distant analysis of the spill further aggrevates an already difficult situation, raising the cost of cleanup further. When dealing with hazardous materials, such delays occasioned by remote analysis introduce the further potential risk to life.

SUMMARY OF THE INVENTION

It is, therefore, a principal object of the present invention to overcome the above shortcomings by providing a portable fluorescence instrument for on-site analysis of oil samples and hazardous materials.

More specifically, it is an object of the present invention to provide a portable fluorescence instrument that records a fluorescence spectrum of a sample on an instant film for immediate on-site identification of the sample of oil or hazardous material.

It is a further object of the present invention to provide a portable fluorescence instrument characterized by fluorescence optics that include a density step tablet which modulates the fluorescence intensity emanating from an excited sample, the modulated fluorescence intensity resulting in a spectral display that is representative of the particular sample.

It is yet another object of the present invention to provide a portable fluorescence instrument characterized by ultraviolet excitation optics that include circuitry which adapts the instrument to field exploration by using low voltage power, obtainable from either an internal rechargeable power source or from a conventional automobile battery, to ignite and power an ultraviolet radiation source.

Briefly, the portable fluorescence instrument of the invention, particularly adapted for on-site analysis of oil samples, comprises excitation optics including a low-pressure mercury lamp whose output, filtered by a short-wave pass filter, provides ultraviolet radiation. Circuitry, using low voltage DC power to ignite and power the lamp, adapts the instrument for field exploration. The ultraviolet radiation is absorbed by most aromatic hydrocarbons which fluoresce. Samples of oil or of hazardous materials (residues, wastes, etc.) are examined either as thin films deposited on a foil tray or as solutions thereof in a suitable solvent and introduced into the instrument in a stoppered cuvette. Fluorescent radiation from an excited sample is passed through a long-wave pass filter and a density step tablet before entering through a slit of a polychromator. The density step tablet modulates the intensity of the fluorescent radiation over the length of the slit. The modulated fluorescence is dispersed by a grating of the polychromator. An instant film, disposed in an instant film cassette, with the film located at the focal plane of the grating, records the dispersed, modulated fluorescence spectrum characteristic of the sample under investigation. Fluorescence intensity information is displayed directly on the print, obviating the need for using an ancillary equipment such as a scanning densitometer to read the point. The instrument is thus a field-deployable fluorescence instrument that permits rapid on-site screening of oil and hazardous materials.

BRIEF DESCRIPTION OF THE DRAWINGS

For a fuller understanding of the nature and objects of the present invention, reference is made to the following specification, which is to be read in reference to the accompanying drawings, wherein.

DETAILED DESCRIPTION OF THE PREFERRED EMBODIMENT

Figure 1:
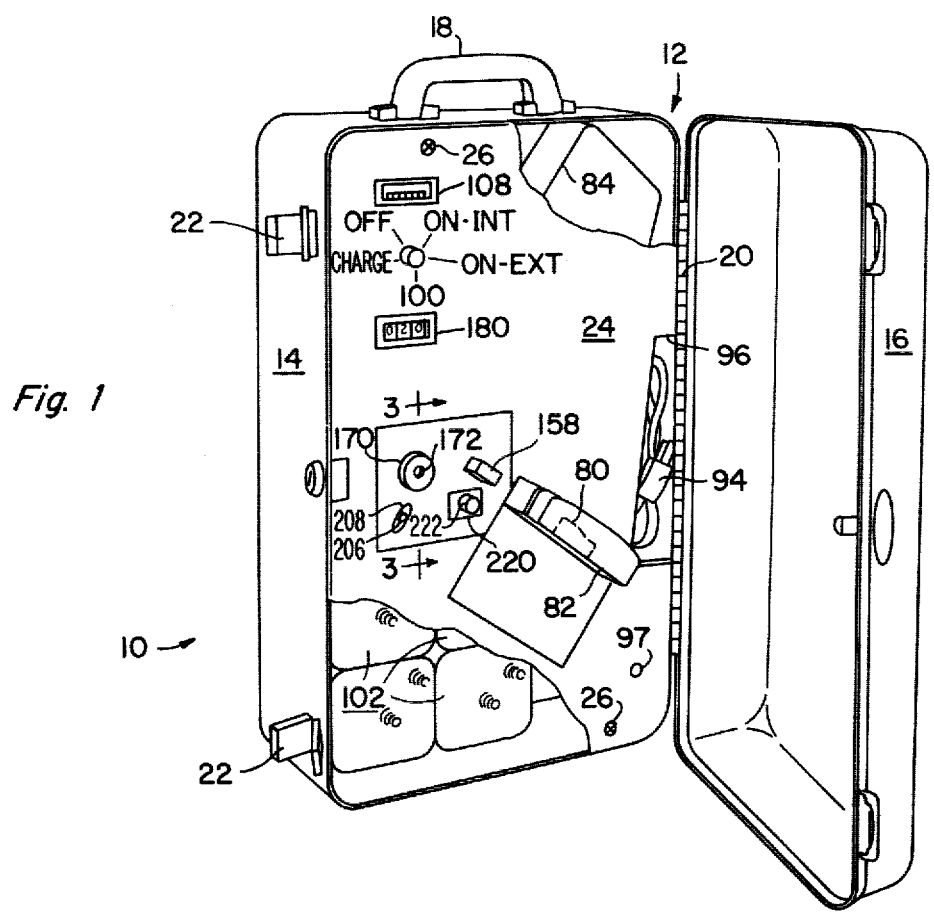
FIG. 1 is a perspective view of a portable fluorescence instrument constructed in accordance with the present invention and contained within a mechanical casing shown in a partially open portion.

A preferred embodiment of a portable fluorescence instrument 10 is shown in perspective in FIG. 1. The portable fluorescence instrument 10 is designed for on-site identification of oil samples and hazardous materials by recording the sample fluorescence spectrum on an instant film. The portable fluorescence instrument 10 is conveninetly contained within a mechanical casing 12 having a body portion 14, a cover portion 16 and a handle 18 secured to the body portion 14. The cover portion 16 is mounted to the body portion 14 by a hinge 20 and is secured in a closed position by a pair of latches 22, 22. A front panel 24 is mounted to body portion 14 by means of a plurality of screws 26.

Figure 2:
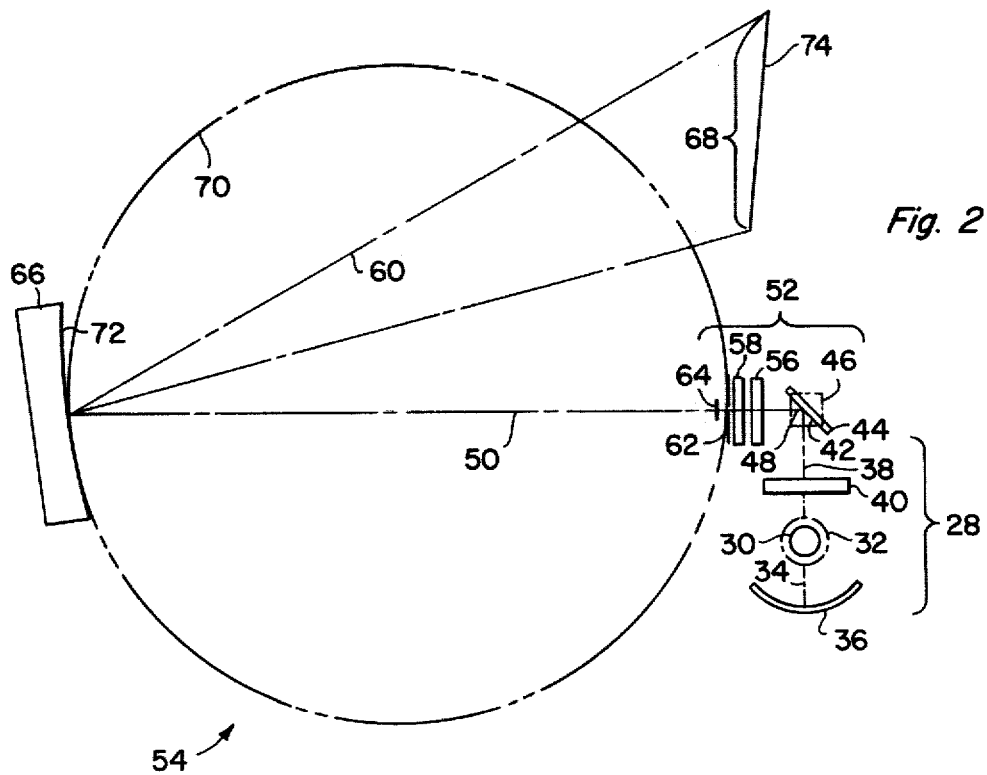
FIG. 2 shows an optical diagram for the portable fluorescence instrument shown in FIG. 1.

The portable fluorescence instrument 10 of the invention essentially comprises ultraviolet excitation optics 28, including a low pressure mercury (Hg) lamp 30 to serve as the ultraviolet radiation (UV) excitation source, note FIG. 2. A first shutter 32 is formed as a sleeve completely surrounding the lamp 30 and is axially displaceable over the lamp 30 so as to allow ultraviolet radiation 34 from the lamp 30 to strike a reflector 36. The reflector 36 directs the ultraviolet radiation 34 in a first path 38 where it is first filtered by a short-wave pass interference filter 40 for isolation of the preferred 254 nm wavelength mercury line to provide the primary excitation. Useful excitation is also available from the same lamp 30 at 313 nm and 365 nm wavelengths (useful for heavy oils) with the use of different interference filters. These particular wavelengths are absorbed by most hydrocarbons which fluoresce. The primary excitation wavelength of 254 nm represents a particularly intense line from the mercury lamp 30.

The ultraviolet radiation 34 still proceeding in the first part 38 is then allowed to strike the front surface of a sample 42 of oil or of a hazardous or toxic material. Samples 42 are preferably examined as thin films deposited on a disposable foil tray 44, using a pipette, a swab or a brush. Samples 42 can also be examined as solutions, using a suitable solvent and introduced into the first path 38 in a stoppered cuvette 46.

Fluorescent radiation 48 emanating from the excited sample 42 is directed towards fluorescence optics 52 and a polychromator 54, which are disposed in a second path 50. The fluorescence optics 52 include a long-wave pass cut-off filter 56 to remove radiation 48 lower than about 280 nm in wavelength. Thus, the wavelength region of the fluorescent radiation 48 passing through the cut-off filter 56 is approximately 280 nm through about 900 nm. The cut-off filter 56 is so constructed, however, that a small amount of the fluorescent radiation 48 is passed below this wavelength region at about 250 nm to allow for wavelength calibration.

Figure 7:
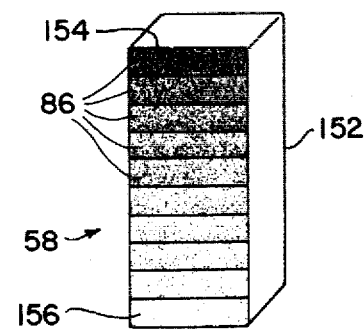
FIG. 7 is a perspective view of a density step tablet used in the portable fluorescence instrument shown in FIG. 1.

The fluorescence optics 52 further include a density step tablet 58 having a plurality of steps 86 (FIG. 7). This density step tablet 58 modulates the intensity of the fluorescent radiation 48 for the same time period and over the band of wavelengths passing through the cut-off filter 56. The density step tablet 58 and its operation will be described in more detail below.

Figure 8:
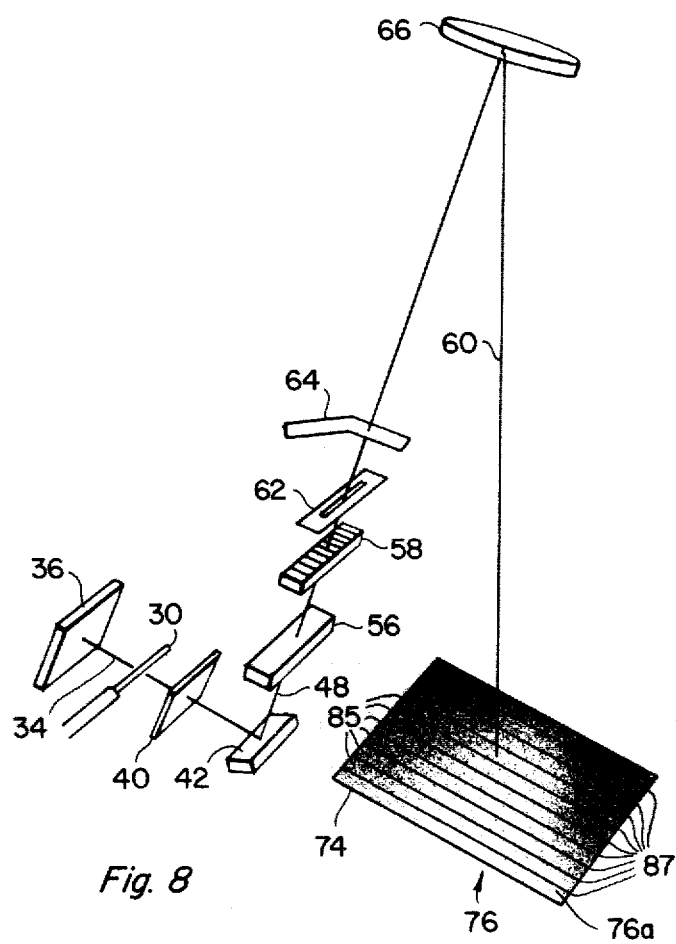
FIG. 8 is a perspective view of excitation and fluorescence optics and of a grating used in the portable fluorescence instrument of FIG. 1 in recording a spectogram of an oil sample on an instant film.

The modulated fluorescent radiation 48 is directed through a slit 62 of the polychromator 54 and a second shutter 64 mounted adjacent the slit 62. The shutters 32 and 64 are operated in synchronism, as will be more apparent from below. The modulated fluorescent radiation 48 admitted through the unobstructed slit 62 is allowed to strike a holographic, flat-field grating 66 designed to be substantially free of aberration and astigmatism. Consequently, the grating 66 has a focal plane 68 which is off a Rowland circle 70. The Rowland circle 70 is a circle whose diameter is equal to the radius of curvature of a grating surface 72 of the grating 66. Normally, and in the absence of using the special grating 66, both the slit 62 and the focal plane 68 would lie on this Rowland circle 70. The grating 66 disperses the modulated fluorescent radiation 48 in a third path 60. An instant film 74, located at the focal plane 68 of the grating 66, records the dispersed modulated fluorescent radiation 48 in path 60 as a spectrogram 76 (observe FIG. 8) characteristic of the sample 42 under examination. The spectrogram 76 is in focus, and exhibits good resolution.

The instant film 74 is disposed in an instant film cassette 80, holding a plurality of prints, with the cassette 80 replaceably introduced into an instant camera back 82 mounted on the front panel 24 of the instrument 10. The camera back 82 is simply the back part of an instant camera after all its optics and shutter mechanism have been removed. Preferably, the camera back 82 is the back of a Polaroid CB-101 Film Camera that accepts 100 or 600 series Polaroid film. Once the instant film cassette 80 is in position within the camera back 82 and with its film safety cover removed, the first film 74 is ready to be exposed by the dispersed modulated fluorescent radiation 60 emanating from the sample 42. For this reason, the excitation optics 28, the sample foil tray 44 or the stoppered cuvette 46, the fluorescence optics 52, the polychromator 54 and the camera back 82 are all disposed within a light tight compartment 84.

The instant that the sample 42 has been excited by ultraviolet radiation 34, the dispersed modulated fluorescent radiation 60 emanating from that sample 42 is being recorded by the instant film 74 in the camera back 82. Due to the modulation effected by the density step tablet 58, the film 74 (observe FIG. 8) records in two dimensions on the spectrogram 76: the first as an exposure (exposure = intensity × time) recording the fluorescence intensity at each wavelength (note lowermost strip 76a), and the second as a progressively decreased fluorescence intensity 85 for each density step 86 of the tablet 58 (observe FIG. 7) for the same wavelengths and for the same time period.

Figure 9:
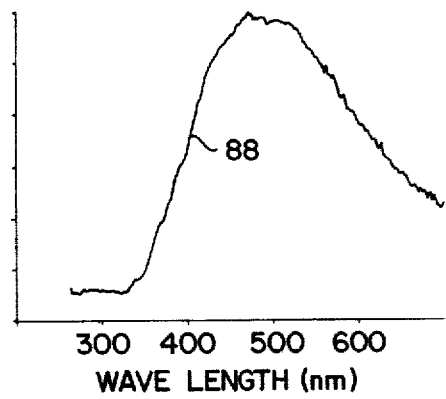
FIG. 9 shows an analog output of a conventional fluorimeter analyzing the same oil sample from which the spectogram of FIG. 8 has been obtained.

Were it not for the use of the density step tablet 58, the film 74 would only show intensity variations versus wavelengths as depicted at the lowermost strip 76a of the spectrogram 76. The tablet 58 filters the intensity of the fluorescent radiation 48 at each wavelength and during the same time period. The use of the density steps 86 of the tablet 58 thus results in the spectrogram 76 that displays directly the intensity information which approximates an analog output 88 of a conventional fluorimeter analysing the same sample 42, observe FIG. 9.

The fluorescence instrument 10 of the invention is rendered truly portable, hence adaptable for field use, by the provision of circuitry 90 that uses low voltage DC power.

Figure 6:
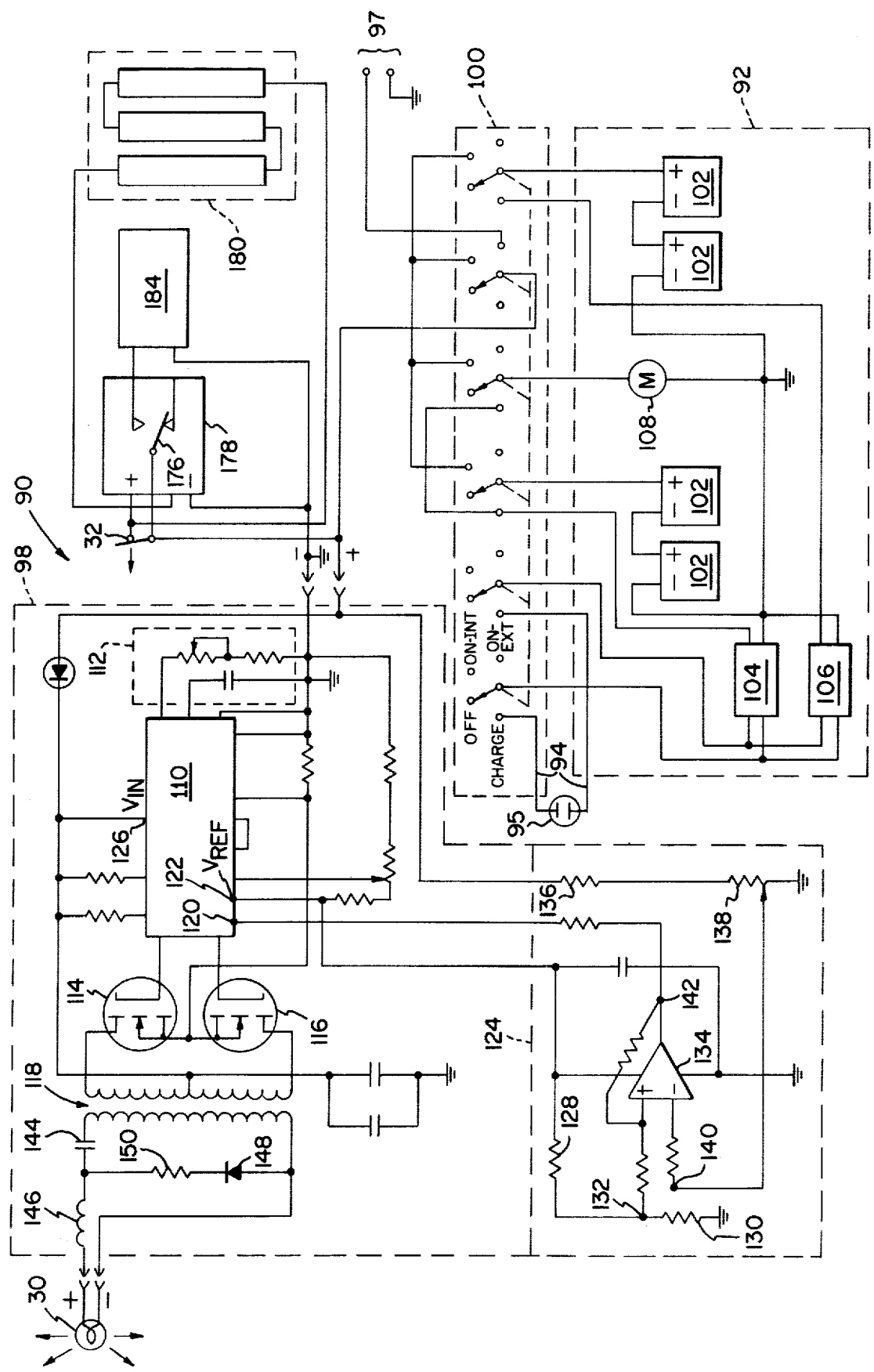
FIG. 6 is a schematic view of a circuitry of the portable fluorescence instrument shown in FIG. 1.

The low pressure mercury lamp 30, used as the UV excitation source, is usually powered from a current limiting and regulating power supply connected to a 115 VAC 60 Hz power source not normally available in the field. Low voltage DC power, however, is not directly usable either to ignite or to power the lamp 30. Hence, the provision of the unique circuitry 90, shown in FIG. 6, that efficiently converts the low voltage DC power to high voltage AC power sufficient both to ignite and to operate the lamp 30. The low voltage DC power is obtainable either from an internal power source 92, rechargeable through an AC recharging cord 94 from a receptacle 95 of a conventional 115 VAC, 60 Hz power source or from a conventional automobile battery via an adaptor cable plugged into an automobile cigarette lighter and a jack 97 provided on the front panel 24. When not in use, the AC recharging cord 94 is accommodated in a retracted position within a channel 96 formed in the front panel 24 adjacent the hinged connection 20 between the body portion 14 and the cover portion 16 of the casing 12.

The circuitry 90 essentially includes, in addition to the internal rechargeable power source 92, a converter 98 to transform the low voltage DC current from source 92 to a high voltage AC current, and a four-position, six pole, rotary switching element 100. Element 100 is designed to connect selectively either the internal power source 92 or an automobile battery via the jack 97 to the converter 98. The converter 98, in turn, ignites the lamp 30 and keeps it on during the instrument's 10 use.

The internal power source 92 comprises one or two pairs of 6 VDC rechargeable batteries 102, for example lantern batteries. Each pair of batteries 102 is connected in series to provide a total of 12 volts. When the switching element 100 is in the charge position and the AC recharging cord 94 is plugged into the receptacle 95 of a 115 VAC 60 Hz power source, each pair of batteries 102 is charged by an individual charger 104 and 106. Battery charging can be observed on a charge indicator 108 located on the front panel 24 just above the switching element 100. The charge indicator 108 is a meter that monitors only one pair of batteries 102 in the CHARGE mode but monitors both pairs of batteries 102 in the ON-INT (i.e., on internal power source 92) mode, observe FIG. 6.

The converter 98 to transform the low voltage DC current to a high voltage AC current includes frequency determining elements 100 and 112 and a pair of switching elements 114 and 116. The frequency determining element 110 is a regulating pulse width modulator integrated circuit used in many low voltage switching type power supplies. The element 110 incorporates an oscillator circuit whose frequency is determined by the RC time constant of the frequency determining element 112. The element 110 drives the pair of switching element 114 and 116. Elements 114 and 116 are metal oxide semiconductor (MOS) type power FET switching transistors. These switching elements 114 and 116 alternately drive a step-up transformer 118 of the ferrite core type. It should be noted that the element 110 generates push-pull output pulses that have a "dead time" between the pulses. Consequently, any switching transients from the transformer 118 and from one of the pair of switching elements 114 and 116 decay before the other of the pair of switching elements 114 and 116 is actuated. The element 110 also has a shut-down circuitry at pin 120 and a voltage reference ($V$REF) at pin 122. A battery voltage sensing circuit 124 is connected to these pins 120 and 122.

When the battery input voltage ($V$IN) at a pin 126 of element 110 drops below a preset value, the converter 98 is automatically shut off by sensing circuit 124. This saves the batteries 102 from being too deeply discharged, a condition which could permanently damage the batteries 102.

The battery voltage sensing circuit 124 includes a fixed attenuator, consisting of resistors 128 and 130, connected to pin 122 ($V$REF) and to one input 132 of an operational amplifier 134 used as a comparator. A variable attenuator, consisting of resistors 136 and 138, is connected to the battery input voltage ($V$IN) and to a second input 140 of the operational amplifier 134. The output 142 of the operational amplifier 134 is in turn coupled to the shutdown circuitry of the element 110 via pin 120.

The characteristics of the low pressure mercury lamp 30 used as the UV excitation source are such that, when ignited, the lamp 30 represents a negative impedance. This requires that the lamp current be limited by a reactive ballast consisting of a capacitor 144 and an inductor 146. In order to ignite the lamp 30, however, a high voltage must be applied. The use of high voltage DC power to ignite and to operate the lamp 30 had been found to be inefficient due to the requirement of using a ballast resistor that would in fact dissipate twice as much power as the lamp 30. A high voltage diode 148 and a resistor 150, connected in parallel with the lamp 30, combine with the capacitor 144 to form a half-wave voltage doubler circuit that provides about 1200 VAC peak voltage across the lamp 30. With the lamp 30 conducting, the current drawn by the lamp 30 is much greater than the current drawn by the diode 148 and the resistor 150. Consequently, the rectifier portion of the voltage doubler is, in effect, no longer in the circuit once the lamp 30 has been ignited.

As already mentioned, the fluorescent radiation 48 emanating from the samples 42 is modulated by the density step tablet 58. The density step tablet 58 is a neutral density step filter that includes a quartz substrate 152 (observe FIG. 7), one side 154 of which has the density steps 86 deposited thereon. The density steps 86 are formed by evaporating varying amounts, as between the steps 86, of a nickel-base alloy containing about 16% chromium and about 7% iron. A bottom step 156, representing step one of ten steps, is clear. The remaining nine density steps 86, counting from the clear bottom step 156 and upward, have ever increasing amounts of the nickel-base alloy evaporated thereon, progressively increasing the densities of each of the steps 86. That is, each density step 86 is distinguishable from each other density step 86 by a different density level. In order to end up with the visual spectrogram 76, characterized by decreased fluorescence intensity bands 85, on the instant film 74 whose response is logarithmic to exposure, one must attenuate linearly with respect to density as between the steps 86, e.g., from one step 86 to its adjacent step 86. Each density step 86 is characterized by a substantially constant density along its entire surface. This results, on the spectrogram 76, in a series of horizontal bars 87 separating the decreased fluorescence intensity bands 85 from each other. The result is the spectogram 76 having bars 87 in a horizontal direction, with the spectrogram 76 displaying the intensity information according to wavelength.

The portable fluorescence instrument 10 is provided with two density step tablets 58, each having its own distinct dynamic range. One dynamic range is the extended range (30:1) having a density range from 0.0 to 1.5. The other dynamic range is the normal range (3:1) having a density range from 0.0 to 0.5. In the extended range, each successive density step 86 upward from the clear bottom step 156 decreases the amount of fluorescent energy reaching the instant film 74 by a factor of 1.41. Two successive density steps 86 decrease the amount of fluorescent energy reaching the film 74 by approximately a factor of 2 (e.g., $1.41^2$). In the normal range (3:1), each successive density step 86 upward from the clear bottom step 156 decreases the amount of fluorescent energy reaching the film 74 by a factor of 1.12. Consequently, in this normal range, it takes six successive density steps 86 to decrease the amount of fluorescent energy reaching the film 74 by a factor 2 (e.g., $1.12^6$).

Figure 3:
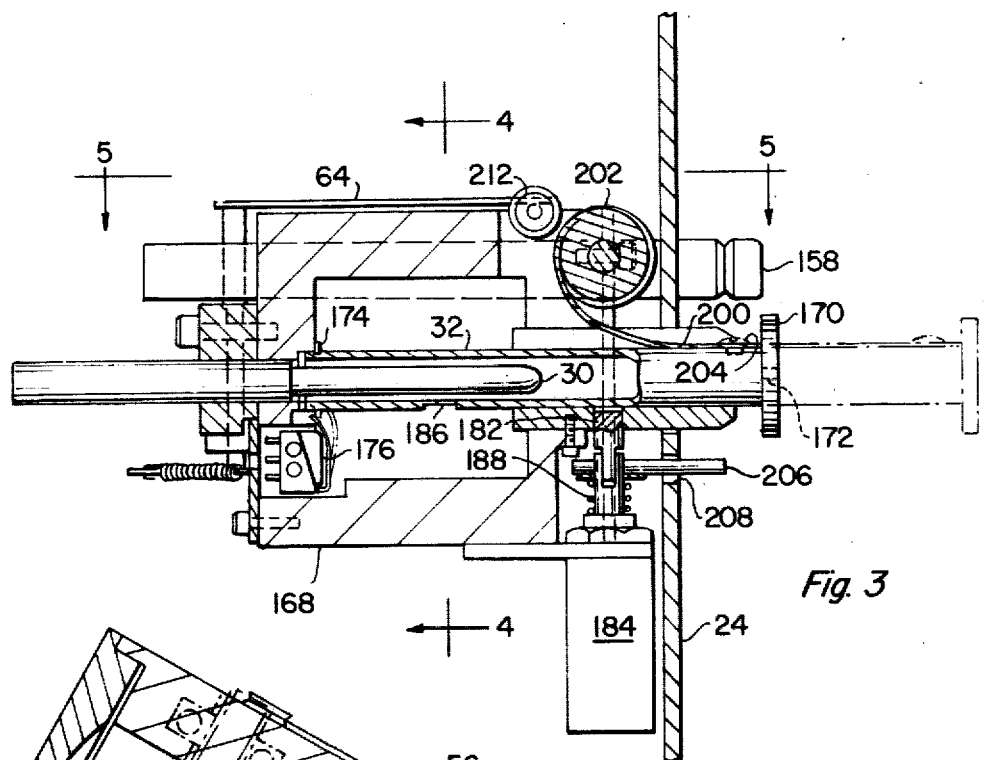
FIG. 3 is a right cross section, partly in elevation, taken along the lines of 3—3 of FIG. 1.
Figure 4:
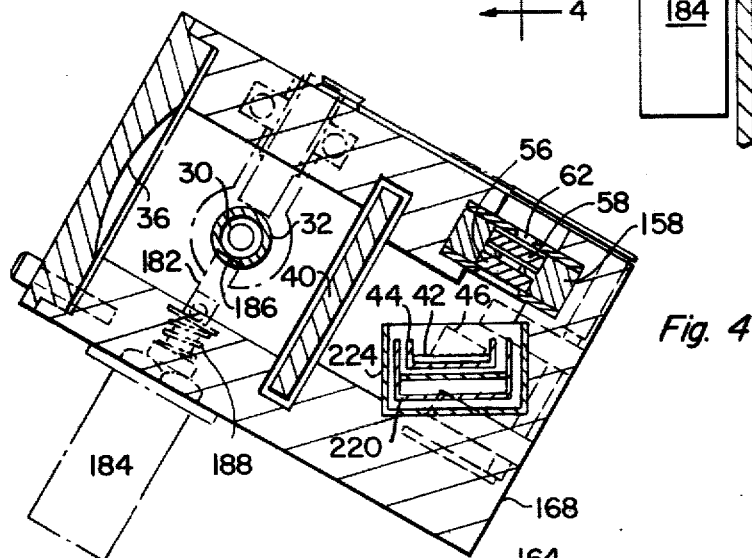
FIG. 4 is a right cross section taken along the lines of 4—4 of FIG. 3.
Figure 5:
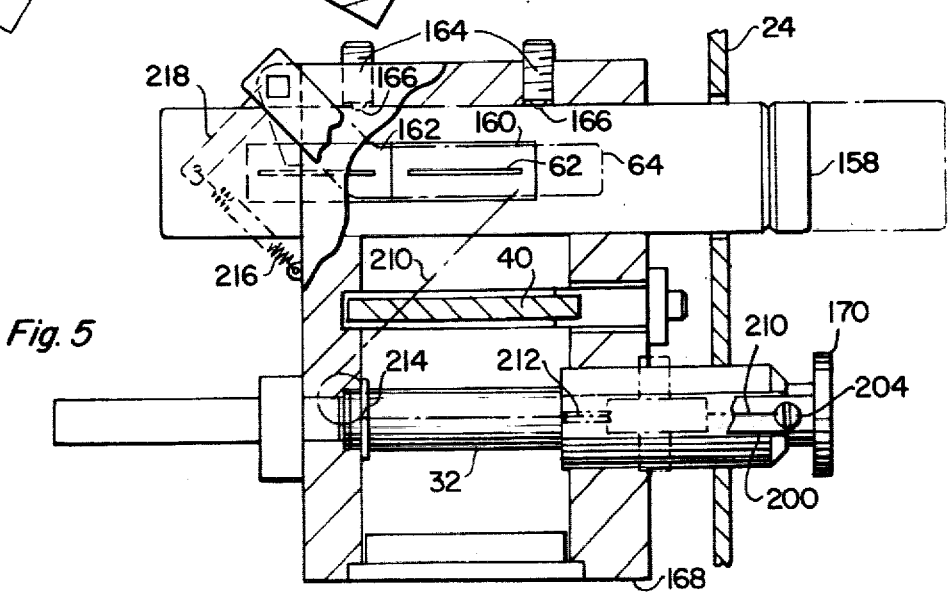
FIG. 5 is a plan view taken along the lines of 5—5 of FIG. 3.

The two density step tablets 58, each with its own long-wave pass filter 56 and slit 62, are removably disposed as two sets within a slide assembly 158 (FIGS. 3, 4 and 5). One set 160, representing the normal dynamic range (3:1), is positioned in the path 50 of the fluorescent radiation 48 with the slide assembly 158 in the position shown in solid lines. This represents the completely in position for the slide assembly 158 with respect to the front panel 24 of the instrument 10. A second set 162, representing the extended dynamic range (30:1), is positioned into the path 50 of the fluorescent radiation 48 with the slide assembly 158 withdrawn from the front panel 24, as shown in phantom lines. A pair of ball plungers 164, cooperating with a pair of detents 166 formed in a side of the slide assembly 158, secure the slide assembly 158 in one or the other of its two operative positions.

Reference is made to FIGS. 3, 4 and 5 which depict certain of the operative parts of the portable fluorescence instrument 10 mounted within a housing 168. The first shutter 32 is provided with a flange 170 having a concentric aperture 172 covered by an ultraviolet filter. When the lamp 30 is on, light can be readily observed through the aperture 172. The lower end of the first shutter 32 is provided with a crescent ring 174 that keeps a microswitch 176 of a timer 178 (observe FIG. 6) in its normally closed position. When the first shutter 32 is opened by an operator pulling its flange 170 away from the front panel 24, the microswitch 176 triggers the timer 178. The time that the timer 178 keeps the shutter 32 open is set on an exposure time select switch 180. This switch 180 is a three-decade push button module that allows exposure times to be selected from 3 seconds to 300 seconds. With the first shutter 32 assuming its open position shown in phantom lines in FIG. 3, it remains locked in the open position by a shaft 182 of a solenoid 184 entering into a depression 186 formed in the shutter 32. The shaft 182 is normally urged against the shutter 32 and for entry into the depression 186 by a compression spring 188 disposed about the shaft 182.

A negator spring 200, wound about a drum 202 on the one hand and secured by a screw 204 to the shutter 32 at its free end, is instrumental in returning the shutter 32 to its normally closed position. When the exposure time set on the switch 180 has expired, the solenoid 184 is actuated to withdraw its shaft 182 from the depression 186. Thereupon, negator spring 200 pulls the first shutter 32 back into the front panel 24 into its normally closed position enveloping the lamp 30. Exposure times less than 3 seconds must be timed manually. Exposure times in excess of 300 seconds are obtained by reopening the shutter 32, thus reactivating the timer 178. A manual release 206 is secured to the shaft 182 and can be displaced thereby within a slot 208 formed in the front panel 24 so as to allow the shutter 32 to be closed by the negator spring 200.

As already mentioned, operation of the second shutter 64 is synchronized with that of the first shutter 32. This is accomplished by securing a cable 210 to the first shutter 32 by the same screw 204 that fastened the negator spring 200 thereto. The cable 210 is wound about an upper pulley 212, a lower pulley 214, and then secured to the second shutter 64, observe FIG. 5. The second shutter 64 is maintained in its normally closed position overlying the slit 62 by a tension spring 216 connected between the housing 168 and an arm 218 secured to the second shaft 64. When the first shutter 32 is opened by pulling it away from the front panel 24, the cable 210 will simultaneously cause the second shutter 64 to be moved away from its blocking position over the slit 62. When the first shutter 32 is closed by being pulled back into the front panel 24 by the negator spring 200, the cable 210 will give and permit the tension spring 216 to return the second shutter 64 to its closed position over the slit 62.

Identification of an oil sample by the portable fluorescence instrument 10 is as follows. Using a clean pipette or brush, a thin layer of about 1 mm of the sample 42 is deposited evenly onto the disposable foil tray 44 placed within a sample drawer 220. The sample drawer 220, having a fluted knob 222, is designed to be introduced into the instrument 10 through the front panel 24 and within a second housing 224 mounted within the housing 168, note FIG. 4. When analyzing dilute solutions of oil or hazardous materials in water or other solvents, the stoppered cuvette 46, contained in a holder, is placed in the drawer 220. For this analysis, the instrument 10 is best placed on its back so that the cuvette 46 is vertical; this avoids the problem of a leak in the stopper.

With the switching element 100 in the ON-INT or ON-EXT position and the exposure time set on the switch 180, the flange 170 of the shutter 32 is pulled away from the front panel 24 until the shutter 32 locks in the extended position. The shutter 32 will automatically close when the preset time has expired or when the manual release 206 is operated. The instant film 74 just exposed is then removed from the camera back 82 and developed, observe FIG. 8. The spectrogram 76 is read by the naked eye for sample identification.

Thus, it has been shown and described a portable fluorescence instrument 10, which satisfies the objects and advantages set forth above, for immediate on-site identification of oils or hazardous materials.

Since certain changes may be made in the present disclosure without departing from the scope of the invention involved herein, it is intended that all matter described in the foregoing specification or shown in the accompanying drawings be interpreted in an illustrative and not in a limiting sense.

What is claimed is:
1. A portable fluorescence instrument contained within a casing and comprising:
 (a) a source for generating radiation in a first path;
 (b) a sample chamber to present samples into said first path;
 (c) a shutter disposed in said first path between said source and said sample chamber;
 (d) said samples, when excited by said radiation from said source, emitting fluorescent radiation in a second path;
 (e) a grating having a focal plane off the Rowland circle and disposed in said second path for dispersing said fluorescent radiation;
 (f) first means disposed in said second path between said sample chamber and said grating to modulate the intensity of said fluorescent radiation striking said grating; and
 (g) second means disposed in said focal plane of said grating off said Rowland circle to record the modulated radiation dispersed by said grating.

2. A portable fluorescence instrument contained within a casing and comprising:
 (a) a source for generating radiation in a first path;
 (b) a sample chamber to present samples into said first path;
 (c) a shutter disposed in said first path between said source and said sample chamber;
 (d) said samples, when excited by said radiation from said source, emitting fluorescent radiation in a second path;
 (e) a grating disposed in said second path for dispersing said fluorescent radiation;
 (f) first means disposed in said second path between said sample chamber and said grating to modulate said fluorescent radiation striking said grating, said first means being a neutral density step filter comprising a substrate having a plurality of steps, with said steps characterized by possessing linearly attenuated densities as between said steps; and (g) second means disposed in the focal plane of said grating to record the modulated radiation dispersed by said grating.

3. The portable fluorescence instrument of claim 2 wherein said attenuation in the densities of said steps is effected by evaporating varying amounts, as between steps, of a nickel-base alloy containing about 16% chromium and about 7% iron on said substrate.

4. The portable fluorescence instrument of claim 1 further including a second shutter, disposed in said second path, said first and second shutters being operated in synchronism, and wherein said second means is an instant film.

5. The portable fluorescence instrument of claim 4 further including a low voltage internal rechargeable power source and an adaptor to a low voltage external power source, with either source being sufficient to power said radiation source.

6. A portable, self-contained fluorescence instrument comprising:
(a) a casing having a body portion, a cover portion and a handle secured to said body portion, said body portion having a panel facing said cover portion, said body portion removably accommodating the operative parts of said instrument behind said panel;
(b) a lamp emitting ultraviolet radiation in a first path;
(c) a shutter disposed in said first path to permit passage of said ultraviolet radiation;
(d) a sample chamber designed to present samples into said first path;
(e) said samples, upon being excited by said ultraviolet radiation, emitting fluorescent radiation in a second path;
(f) a slit and a grating disposed in said second path, said grating for dispersing said fluorescent radiation;

(g) a neutral density step filter disposed in said second path between said sample chamber and said slit to modulate said fluorescent radiation entering said slit; and
(h) means disposed in the focal plane of said grating to record the radiation dispersed by said grating.

7. The portable, self-contained fluorescence instrument of claim 6 wherein said grating is a flat-field, holographic grating, substantially free of aberration and astigmatism and having a focal plane off the Rowland circle.

8. The portable, self-contained fluorescence instrument of claim 6 wherein said body portion is provided with a light-tight compartment.

9. An optical system for use in a fluorescence instrument, said system comprising:
(a) excitation optics including a radiation source, circuitry having a low voltage portable power source to power said radiation source, and a filter to filter the radiation from said radiation source;
(b) means to present a sample into the path of said radiation from said radiation source to excite said sample to fluoresce in a second path; and
(c) fluorescence optics disposed in said second path and including a density step tablet to modulate the fluorescent radiation emanating from said sample.

10. The optical system of claim 9 wherein said radiation source is a low pressure mercury lamp.

11. The optical system of claim 9 wherein said density step tablet is a neutral density step filter comprising a substrate having a plurality of steps, with said steps characterized by possessing linearly attenuated densities as between said steps.

12. The optical system of claim 11 wherein said attenuation in the densities of said steps is effected by evaporating varying amounts, as between said steps, of a nickel-base alloy containing about 16% chromium and about 7% iron on said substrate.

* * * * *